(12) United States Patent
Cobb et al.

(10) Patent No.: US 6,500,151 B1
(45) Date of Patent: Dec. 31, 2002

(54) SYRINGE PUMP

(75) Inventors: Anthony Richard Cobb, Brighton (GB); Robert James Tribe, Loughton (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 09/537,084

(22) Filed: Mar. 29, 2000

(30) Foreign Application Priority Data

Apr. 28, 1999 (GB) ................................ 9909654

(51) Int. Cl.[7] .................. A61M 37/00; A61M 31/00
(52) U.S. Cl. .................. 604/131; 604/93.01; 604/48
(58) Field of Search .................. 250/237; 604/67, 604/152, 208, 154, 50, 155, 131; 705/3; 664/67; 73/19.08; 205/231.14

(56) References Cited

U.S. PATENT DOCUMENTS

| | | | |
|---|---|---|---|
| 4,384,204 A | * | 5/1983 | Tamaki et al. .......... 250/231.18 |
| 4,529,401 A | | 7/1985 | Leslie et al. |
| 4,627,835 A | * | 12/1986 | Fenton, Jr. .............. 128/DIG. 1 |
| 4,741,732 A | * | 5/1988 | Crankshaw et al. ......... 604/155 |
| 4,804,368 A | * | 2/1989 | Skakoon et al. ........ 128/DIG. 1 |
| 4,838,857 A | * | 6/1989 | Strowe et al. ....... 128/DIG. 12 |
| 4,976,696 A | * | 12/1990 | Sanderson et al. ... 128/DIG. 12 |
| 5,097,122 A | * | 3/1992 | Colman et al. ......... 250/231.14 |
| 5,232,449 A | * | 8/1993 | Stern et al. ............. 128/DIG. 1 |
| 5,425,716 A | * | 6/1995 | Kawasaki et al. ... 128/DIG. 12 |
| 5,533,981 A | * | 7/1996 | Mandro et al. ............. 604/208 |
| 5,545,140 A | * | 8/1996 | Conero et al. ......... 128/DIG. 1 |
| 5,576,499 A | * | 11/1996 | Davies ........................ 73/433 |
| 5,814,015 A | * | 9/1998 | Gargano et al. ............ 604/151 |
| 6,082,174 A | * | 7/2000 | Lee et al. .................. 73/19.08 |
| 6,269,340 B1 | * | 7/2001 | Ford et al. ..................... 604/19 |

FOREIGN PATENT DOCUMENTS

| | | |
|---|---|---|
| EP | 0 323 321 | 7/1989 |
| EP | 0 514 907 | 11/1992 |
| EP | 0 589 328 | 3/1994 |
| WO | WO 88/10383 | 12/1988 |

OTHER PUBLICATIONS

Hirschman et al, Ecoding of syringe information, US 2001/0034506, US Patent Office, Oct. 25, 2001.*

* cited by examiner

*Primary Examiner*—Brian L. Casler
*Assistant Examiner*—Roz Ghafoorian
(74) *Attorney, Agent, or Firm*—Connolly Bove Lodge & Hutz, LLP

(57) ABSTRACT

A syringe pump has an arm swung against the barrel of the syringe. The arm is coupled to a strip mask having a row of transparent apertures of differing length. The mask extends above a CCD array of sensing elements and below a concave mirror, which produces a collimated beam of radiation on the mask from an LED. The length of sensing elements exposed to radiation through an aperture in the mask gives an approximate indication of barrel size; the position of an edge of the aperture gives an accurate indication. The pump compares the barrel size with information relating size to syringe type and produces an indication of syringe type on a display.

11 Claims, 2 Drawing Sheets

SYRINGE PUMP

BACKGROUND OF THE INVENTION

This invention relates to syringe pumps.

Syringe pumps are used to supply medication to a patient. A syringe is pre-filled with the medication and this is connected to an infusion line extending to the patient. The syringe is then loaded in the syringe pump, which applies a force to the plunger of the syringe to drive medication into the infusion line at a controlled rate. The user enters information about the size of the syringe and the dose rate, so that the pump can calculate the drive rate for the plunger to dispense medication at the correct rate.

Syringe pumps may include a syringe barrel sensor, which provides a measure of the diameter of the syringe loaded in the pump. A display is derived from the output from the barrel size sensor so that the user can-check that he has correctly identified the syringe. The Series 3000 syringe pump sold by SIMS Graseby of Watford, England includes a syringe barrel sensor having an arm that is swung into contact with the outside of the barrel. The arm is coupled to a mask that is movable between a row of five LEDs and a row of five photodiodes. The outputs of the photodiodes give an indication of the position of the mask and hence the size of the barrel of the syringe. Such an arrangement gives an approximate indication of the size of the syringe but is not sufficiently accurate to distinguish, for example, between two syringes from different manufacturers having similar external diameters.

BRIEF SUMMARY OF THE INVENTION

It is an object of the present invention to provide an alternative syringe pump.

According to the present invention there is provided a syringe pump including means for mounting a syringe, means for engaging and driving a plunger of the syringe, and a sensor mechanism for sensing the barrel size of the syringe, the sensor mechanism including a contact member displaceable into contact with the outer surface of the barrel, a mask member coupled with the contact member and movable in response to movement of the contact member, and a row of a plurality of optical sensing means positioned to receive radiation transmitted by the mask member, the mask member including a plurality of transmitting regions arranged in a row, each transmitting region having a different length, and the pump including means responsive to the outputs from the sensors to determine the size of the barrel from the combination of the length of the row of sensing means receiving radiation transmitted by one of the transmitting regions and the position of an edge of the transmitting region.

The transmitting regions are preferably transparent apertures in the mask member. The pump may include a radiation source mounted on the same side of the mask member as the sensing means. The pump may include means for collimating radiation falling on the mask member, such as a concave reflector. The contact member is preferably on a swung arm, which may be rotatable about an axis parallel to the axis of the syringe. The mask member is preferably an elongate strip and the row of transmitting regions preferably extends along the length of the strip. The mask member may have five transmitting regions and the row of optical sensing means may be provided by a CCD array. The pump preferably includes information of the barrel size of different syringes such that the syringe type used can be identified from its barrel diameter, and the pump may include a display on which the syringe type is displayed.

A syringe pump according to the present invention will now be described, by way of example, with reference to the accompanying drawings.

DETAILED DESCRIPTION OF THE PREFERRED EMBODIMENT

Figure 1:
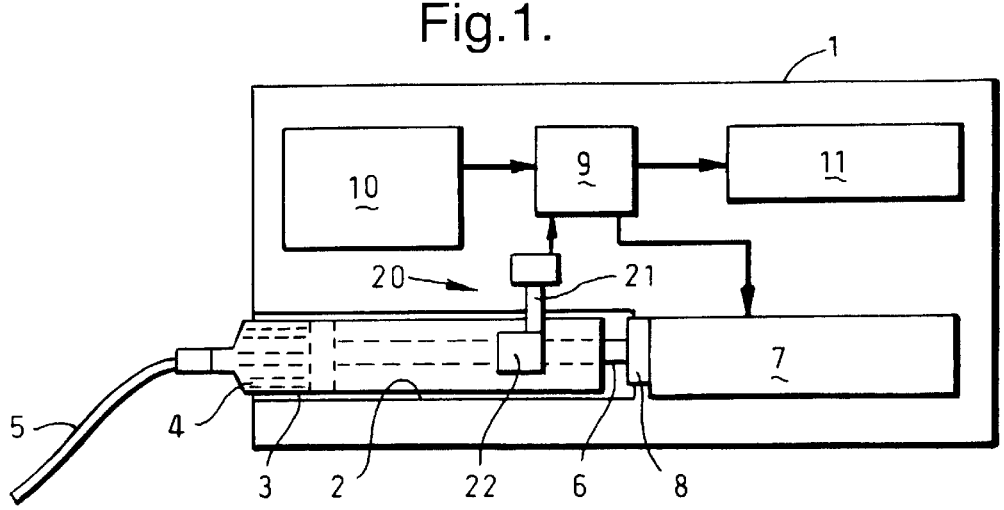
FIG. 1 illustrates the pump schematically.

With reference first to FIG. 1, the pump includes an outer housing 1 with a recess 2 on its front surface shaped to receive a syringe 3 of conventional kind and which may be of a variety of different sizes. The syringe 3 contains a medication liquid 4 that is dispensed to a patient via an infusion line 5 by pushing in the plunger 6 of the syringe. The pump has a conventional drive mechanism 7, such as including a lead screw driven by a motor, coupled with an engaging mechanism for engaging the head 8 of the plunger 6. The drive mechanism 7 is driven by a control unit 9, which receives inputs from a keypad 10, or other user input means, and from a syringe barrel size sensor mechanism 20, which is described in detail below. The control unit 9 also provides an output to a display 11.

Figure 3:
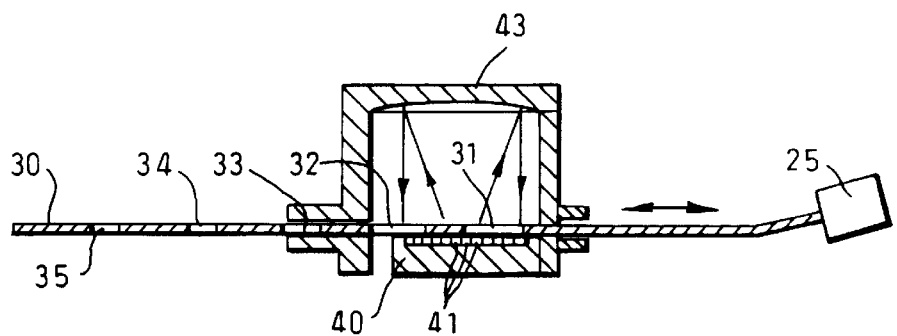
FIG. 3 is a side elevation view of the syringe barrel sensor.
Figure 4:
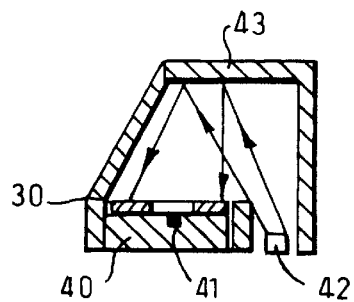
FIG. 4 is an elevation view from one end of the syringe barrel sensor.
Figure 2:
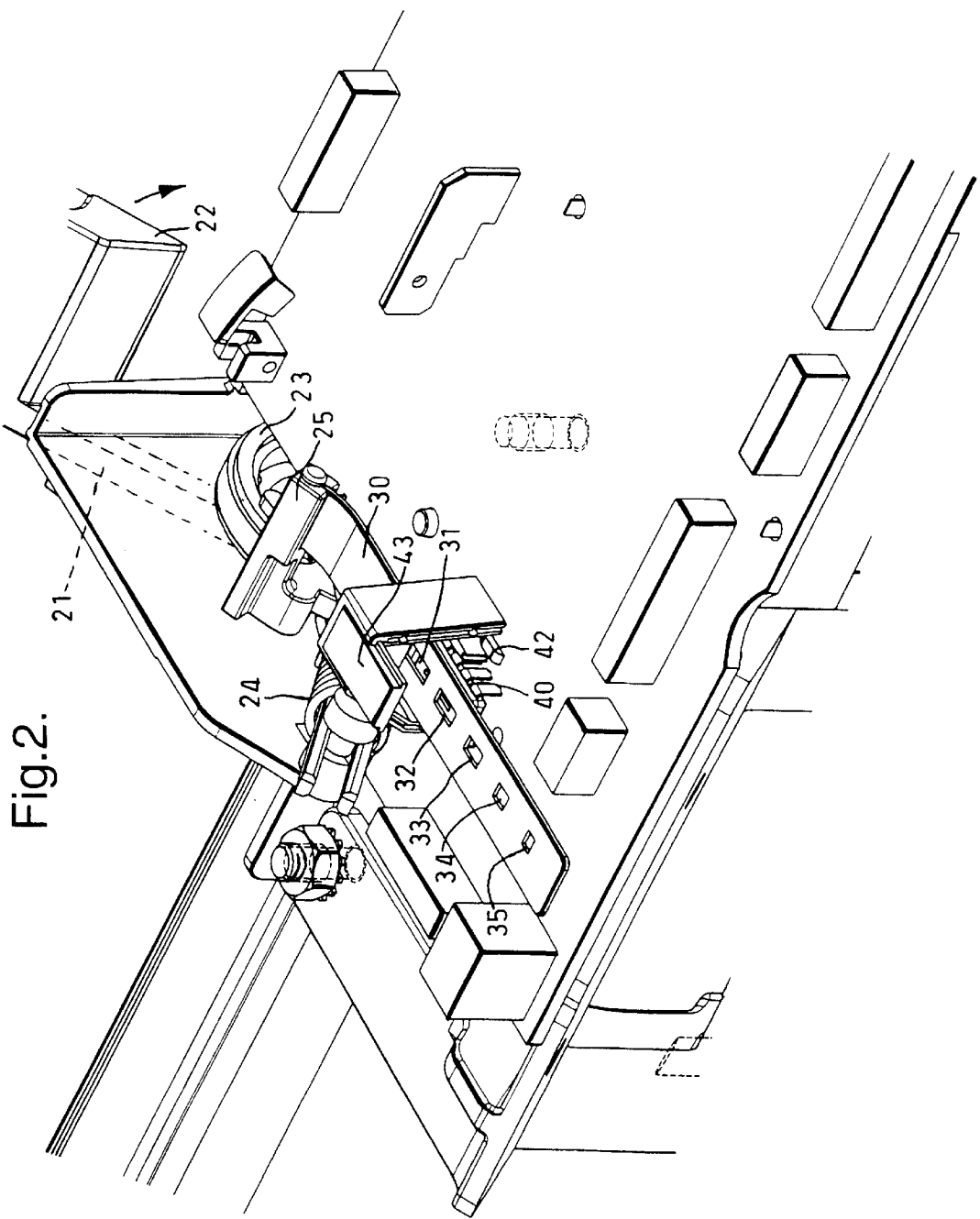
FIG. 2 is a perspective view of a part of the pump with its interior exposed to show the syringe barrel sensor.

With reference now also to FIGS. 2 to 4, the syringe barrel size sensor mechanism 20 includes a swung arm 21 mounted at one end on a shaft (not shown) extending parallel to and to one side of the axis of the syringe 3 so that the arm is rotatable about an axis parallel to the axis of the syringe. The other end of the arm has a contact finger 22 positioned to contact the outside of the barrel of the syringe 3. The shaft of the mechanism 20 is connected axially to a freely rotatable ring 23. A coiled spring 24 connected with the ring 23 urges it in a sense such that the arm 21 swings down until its finger 22 contacts the syringe barrel. The ring 23 has a rod retainer 25 at the edge of the ring projecting parallel to the axis of rotation of the ring. The retainer 25 secures one end of a mask 30 extending generally transverse to the syringe axis. It will be appreciated that rotation of the arm 21 will cause a corresponding rotation of the ring 23 and a linear movement of the mask 30 along its length.

The mask 30 comprises a stiff strip of opaque material, such metal or plastics, having a row or series of five apertures 31 to 35 spaced apart from one another along the length of the mask. The apertures 31 to 35 are of rectangular shape, each having the same width. The length, however, of each aperture 31 to 35 along the mask differs one from the other.

The mask 30 extends lengthways above an optical sensor in the form of a CCD array 40. The CCD array 40 comprises a row of 103 individual sensor elements or pixels 41 extending along its length. The length of the array 40 is greater than that of the longest one of the apertures 31 in the mask 30. The output of the array 40 is supplied to the control unit 9. An LED 42 is mounted below and to one side of the mask 30 and is oriented to direct its radiation upwardly. A concave mirror 43 mounted vertically above the mask 30 is positioned to be illuminated by the LED 42. The optical properties of the concave mirror 43 are such that it reflects a beam of radiation, collimated in a plane including the length of the mask 30, vertically downwardly onto the mask 30 and hence onto any of the pixels 41 of the CCD array 40 exposed through apertures 31 to 35 of the mask. Because the radiation illuminating the CCD array 40 is collimated, it ensures that sharply-defined shadows are produced by the edges of the apertures 31 to 35. The output of the CCD array 40 is a series of analogue signal levels each representing the level of light falling on different ones of the elements 41. This is clocked out of the CCD array 40 and supplied to the control unit 9, which compares the level on each element 41 to determine whether or not the element is illuminated through an aperture 31 to 35 or is shadowed by opaque regions of the mask 30. The control unit 9 performs an algorithm that reads the outputs of the elements 41 it turn to determine where dark changes to light and where it changes to dark again. This provides information on the length of the aperture 31 to 35 through which light falls on the array 40 so that the particular aperture above the array can be identified to give an approximate, unique indication of the position of the mask 30. The position of the boundary between the light and dark regions defines the edge of the aperture 31 to 35 and this enables the position of the mask 30 to be determined with high accuracy. Determining the position of the mask 30 from the edge boundary alone, however, would not give a unique indication of mask position.

FIG. 2 shows the arm 21 raised to its maximum extent for syringes 3 of the largest size, and the mask 30 is shown at one end of its travel, with the longest of the apertures 31 positioned above the array 40. For smaller syringes, the arm 21 has a lower position and the mask is pulled through the array 40 to a different position. The assembly is calibrated by inserting two circular bars, in place of a syringe, the bars having different, known diameters at opposite ends of the range of syringe sizes. This information may be used in a linear equation, a look-up table or a combination of both to determine the size of syringes of other diameters. The face of the finger 22 contacting the syringe barrel is profiled such as to linearize the output of the array 40.

The present invention enables the diameter of syringe barrels to be measured to high accuracy, typically to about 0.4mm. This accuracy is sufficient to enable a majority of current syringes to be identified uniquely and enables syringes from different manufacturers to be distinguished one from the other, even when these have the same nominal capacity. The control unit 9 contains a library of different syringes and information as to their diameters. The output from the array 40 is used to calculate the diameter of the syringe 3 and this is compared against the table to determine which syringe is loaded. The control unit 9 provides a signal to the display 11 indicating the identity of the syringe loaded, for example "Baxter 10 ml", and prompts the user to confirm that this is correct by pressing an appropriate key on the keypad 10. Alternatively, the pump could utilize the information about syringe size as a check against information input to the pump by the user.

The present invention enables improved safety in the use of syringe pumps since there is less risk that the user will incorrectly enter details of the syringe and hence that the pump will dispense an inappropriate dose.

It will be appreciated that the invention could be modified in various different ways, especially as to the manner of illumination of the mask. It is not essential that the mask be a straight strip, it could be curved if appropriately curved sensor arrays are available. The mask member could have transmitting regions formed by reflective regions, rather than by transparent regions. The contact member engaging the outside of the barrel could be movable linearly rather than rotatably.

What we claim is:

1. A syringe pump comprising:
   a mechanism for engaging and driving a plunger of a syringe; and
   a sensor mechanism for sensing a size of a barrel of the syringe, said sensor mechanism comprising:
   a contact member displaceable into contact with said barrel,
   a mask member, having at least a first side, coupled with said contact member and movable in response to movement of said contact member, and
   a row of a plurality of optical sensors positioned to receive radiation transmitted by the mask member, wherein the mask member includes a plurality of transmitting regions arranged in a row, each transmitting region having a different length, and wherein the pump includes a control unit responsive to at least one output from said sensors, said control unit determining the size of the barrel from a combination of a length of the row of sensors receiving radiation transmitted by one of the transmitting regions and a position of an edge of the transmitting region.

2. A pump according to claim 1, wherein the transmitting regions are transparent apertures in the mask member.

3. A pump according to claim 1, wherein said radiation source and said sensors are mounted on said first side of said mask member.

4. A pump according to claim 1, including a collimator for collimating radiation falling on the mask member.

5. A pump according to claim 4, wherein the collimator is a concave reflector.

6. A pump according to claim 1, wherein the contact member is on a swung arm.

7. A pump according to claim 6, wherein the arm is rotatable about an axis extending parallel to the axis of the syringe.

8. A pump according to claim 1, wherein said mask member is an elongate strip and the row of transmitting regions extends along a length of said strip.

9. A pump according to claim 1, wherein the row of optical sensors is provided by a CCD array.

10. A pump according to claim 1, wherein said control unit includes information as to the barrel size of different syringes, and wherein the control unit provides an output to a display on which an identity of the syringe is displayed.

11. A syringe pump comprising: a mechanism for engaging and driving a plunger of a syringe; and a sensor mechanism for sensing a size of a barrel of the syringe, the sensor mechanism comprising a contact member displaceable into contact with the barrel, an elongate mask member coupled with the contact member and movable along its length to a position dependent on the position of the contact member, said mask member having a plurality of transparent apertures spaced along a length of the mask, each said aperture having a different length, a row of a plurality of optical sensors positioned under the mask member, a radiation source arranged to direct radiation onto the sensors through the apertures in the mask such that the length of the row of optical sensors receiving radiation is dependent on the aperture located above the sensors and thereby gives an approximate indication of mask position and barrel size, and such that the position of an edge of the aperture gives a more accurate indication of position and barrel size.

* * * * *